(12) United States Patent
Goodman et al.

(10) Patent No.: US 6,399,042 B1
(45) Date of Patent: Jun. 4, 2002

(54) 4-FLUOROALKYL-3-HALOPHENYL NORTROPANES

(75) Inventors: Mark M. Goodman, Atlanta, GA (US); Ping Chen, Indianapolis, IN (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 09/558,916

(22) Filed: Apr. 26, 2000

Related U.S. Application Data (60) Provisional application No. 60/131,104, filed on Apr. 26, 1999.

(51) Int. Cl.$^7$ .................. A61K 51/00; C07D 451/02
(52) U.S. Cl. ................ 424/1.85; 424/1.89; 546/124; 546/132
(58) Field of Search .................. 424/1.85, 1.89; 546/124, 132

(56) References Cited

U.S. PATENT DOCUMENTS

| 5,310,912 A | * | 5/1994 | Neumeyer et al. | 424/1.85 |
| 5,413,779 A | | 5/1995 | Kuhar et al. | 424/1.85 |

FOREIGN PATENT DOCUMENTS

| WO | 97/43285 | 11/1997 | C07D/451/02 |

OTHER PUBLICATIONS

Blough et al. "Synthesis and Transporter Binding Properties of 3β–(4'–Alkyl–, 4'–alkeny;–, and 4'alkynylphenyl)nortropane–2β–carboxylic Acid Methyl Esters: Serotonin Transporter Selective Analogs" (1996) *J. Med. Chem.* 39(20):4027–4035.

Blough, B.E. et al. "3β–(4–Ethyl–3–iodophenyl)nortropane–2β–carboxylic Acid Methyl Ester as a High–Affinity Selective Ligand for the Serotonin Transporter" (1997) *J. Med. Chem.* 40(24):3861–3864.

Goodman, M.M. *Clinical Positron Emission Tomography* Mosby Yearbook, 1992, K.F. Hubner et al., Chapter 14 "Automated Synthesis of Radiotracers for PET Applications".

Hubner, K.F. *Clinical Positron Emission Tomography* Mosby Year Book, 1992, K.F. Hubner, et al., Chapter 2 "University of Tennessee Biomedical Imaging Center and Transfer of Technology to the Clinical Floor".

Hume, et al. "Citalopram: Labelling with Carbon–11 and Evaluation in Rat as a Potential Radioligand for In Vivo PET Studies of 5–HT Re–uptake Sites" (1991) *Nucl. Med. Biol.* 18:339–351.

Kilbourn et al. "Synthesis of Radiolabeled Inhibitors of Presynaptic Monoamine Uptake Systems: [$^{18}$F]GBR 13119(DA),[$^{11}$C]Nisoxetine (NE), and [$^{11}$C]Fluoxtine (5–HT)" (1989) *J. Label. Cmpd. Radiopharm.* 26:412–414. (Symposium Abstract).

Maryanoff et al. "Pyrroloisoquinoline Antidepressants. In–Depth Exploration of Structure–Activity Relationships" (1987) *J. Med. Chem.* 30:1433–1454.

Mathis et al. "Synthesis and Biological Evaluation of a PET Radioligand for Serotonin Uptake Sites: [F–18] 5–Fluoro–6–Nitroquipazine" (1993) *J. Nucl. Med.* 34:7P–8P.

Murphy, D.L. et al. "Use of Serotonergic Agents in the Clinical Assessment of Central Serotonin Function" (1986) *J. Clin. Psychiatr.* 47(supp)9–15.

Suehiro et al. "Radiosynthesis and Evaluation of N–(3–[$^{18}$F] Fluoropropyl) paroxetine as a Radiotracer for In Vivo Labeling of Serotonin Uptake Sites by PET" (1991) *Nucl. Med. Biol.* 18:791–796.

Suehiro et al. "Synthesis of a Radiotracer for Studying Serotonin Uptake Sites with Positron Emission Tomography: [$^{11}$C]McN–5652–Z" (1992) *J. Label Cmpd. Radiopharm.* 31:841–848.

Suehiro et al. "A PET Radiotracer for Studying Serotonin Uptake Sites: Carbon–11–McN–5652Z" (1993) *J. Nucl. Med.* 34:120–127.

\* cited by examiner

*Primary Examiner*—Michael G. Hartley
(74) *Attorney, Agent, or Firm*—Greenlee, Winner and Sullivan, P.C.

(57) ABSTRACT

A series of compounds in the 4-fluoroalkyl-3-halophenyl nortropanes family are described as diagnostic and therapeutic agents for diseases associated with serotonin transporter dysfunction. These compounds bind to serotonin transporter protein with high affinity and selectivity. The invention provides methods of synthesis which incorporate radioisotopic halogens at a last step which permit high radiochemical yield and maximum usable product life. The radiolabeled compounds of the invention are useful as imaging agents for visualizing the location and density of serotonin transporter by PET and SPECT imaging.

23 Claims, 6 Drawing Sheets

4-FLUOROALKYL-3-HALOPHENYL NORTROPANES

CROSS REFERENCE TO RELATED APPLICATIONS

This application claims priority from U.S. Provisional Application No. 60/131,104, filed Apr. 26, 1999.

ACKNOWLEDGEMENT OF FEDERAL RESEARCH SUPPORT

This invention was made, at least in part, with funding from the United States Department of Energy under contract #DE-FG02-97ER-62367. Accordingly, the U.S. government may have certain rights in this invention.

BACKGROUND OF THE INVENTION

The invention includes novel chemical compounds having specific binding in a biological system and capable of being used for positron emission tomography (PET) and single photon emission (SPECT) imaging methods.

The ability of analog compounds to bind to localized ligands within the body makes it possible to utilize such compounds for in situ imaging of the ligands by PET, SPECT and similar imaging methods. In principle, nothing need be known about the nature of the ligand, as long as binding occurs, and such binding is specific for a class of cells, organs, tissues or receptors of interest. PET imaging is accomplished with the aid of tracer compounds labeled with a positron-emitting isotope (Goodman, M. M. *Clinical Positron Emission Tomography*, Mosby Yearbook, 1992, K. F. Hubner et al., Chapter 14). For most biological materials, suitable isotopes are few. The carbon isotope,[$^{11}$C], has been used for PET, but its short half-life of 20.5 minutes limits its usefulness to compounds that can be synthesized and purified quickly, and to facilities that are proximate to a cyclotron where the precursor [$^{11}$C] starting material is generated. Other isotopes have even shorter half-lives. [$^{13}$N] has a half-life of 10 minutes and [$^{15}$O] has an even shorter half-life of 2 minutes. The emissions of both are more energetic than those of [$^{11}$C]. Nevertheless, PET studies have been carried out with these isotopes (Hubner, K. F., in *Clinical Positron Emission Tomography*, Mosby Year Book, 1992, K. F. Hubner, et al., Chapter 2). A more useful isotope,[$^{18}$F], has a half-life of 110 minutes. This allows sufficient time for incorporation into a radio-labeled tracer, for purification and for administration into a human or animal subject. In addition, facilities more remote from a cyclotron, up to about a 200 mile radius, can make use of [$^{18}$F] labeled compounds. Disadvantages of [$^{18}$F] are the relative scarcity of fluorinated analogs that have functional equivalence to naturally-occurring biological materials, and the difficulty of designing methods of synthesis that efficiently utilize the starting material generated in the cyclotron. Such starting material can be either fluoride ion or fluorine gas. In the latter case only one fluorine atom of the bimolecular gas is actually a radionuclide, so the gas is designated $^{18}$F-F. Reactions using $^{18}$F-F as starting material therefore yield products having only one half the radionuclide abundance of reactions utilizing K$^{18}$F as starting material. On the other hand, [$^{18}$F] can be prepared in curie quantities as fluoride ion for incorporation into a radiopharmaceutical compound in high specific activity, theoretically 1.7 Ci/nmol using carrier-free nucleophilic substitution reactions. The energy emission of [$^{18}$F] is 0.635 MeV, resulting in a relatively short, 2.4 mm average positron range in tissue, permitting high resolution PET images.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analog binding, localization and clearance rates. A useful isotope for SPECT imaging is [$^{123}$I], a γ-emitter with a 13.3 hour half life. Compounds labeled with [$^{123}$I] can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Use of [$^{18}$F] labeled compounds in PET has been limited to a few analog compounds. Most notably, [$^{18}$F]-fluorodeoxyglucose has been widely used in studies of glucose metabolism and localization of glucose uptake associated with brain activity. [$^{18}$F]-L-fluorodopa and other dopamine receptor analogs have also been used in mapping dopamine receptor distribution.

Other halogen isotopes can serve for PET or SPECT imaging, or for conventional tracer labeling. These include $^{75}$Br, $^{76}$Br, $^{77}$Br and $^{82}$Br which have usable half-lives and emission characteristics. In general, the chemical means exist to substitute any halogen moiety for the described isotopes. Therefore, the biochemical or physiological activities of any halogenated homolog of the described compounds are now available for use by those skilled in the art, including stable isotope halogen homologs. Astatine can be substituted for other halogen isotopes; [$^{210}$At] emits alpha particles with a half-life of 8.3 h. At-substituted compounds are therefore useful for tumor therapy, where binding is sufficiently tumor-specific.

Serotonin transporters (SERTs) are proteins that reside on the membrane of the nerve terminals of the serotoninergic neurons. The SERT serves to remove serotonin from the synapse, a process which helps regulate central nervous system (CNS) serotonin neurotransmission. The serotonin transporter has been convincingly implicated in the pathophysiology of major depression and represents the putative sites of action of the majority of the older and newer generation antidepressants [Murphy, D. L. et al. (1986) *J. Clin. Psychiatr.* 47:(suppl)9–15]. Abnormalities in SERT density in the midbrain and frontal cortex has also been associated with obsessive compulsive disorder. Supporting evidence has, however, been indirect resulting from the study of postmortem tissue and animal and peripheral cell models of transporter cell function and pharmacology. Emission tomography techniques present unique opportunities to define the functional status and pharmacology in the living human brain. The development of serotonin transporter imaging agents labeled with positron emitters has been of recent interest as probes to study the roles of the neuroregulatory site using positron emission tomography (PET) and single-photon emission tomography (SPECT).

Currently, there does not exist a single radiopharmaceutical that can be labeled with either fluorine-18 and iodine-123 amenable for regional distribution that is efficacious in differentiating major depression from other psychiatric disorders. Citalopram [Hume et al. (1991) *Nucl. Med. Biol.* 18:339–351], paroxetine [Suehiro et al. (1991) *Nucl. Med. Biol.* 18:791–796], fluoxetine [Kilbourn et al. (1989) *J. Label. Cmpd. Radiopharm.* 26:412–414], and nitroquipazine [Mathis et al. (1993) *J. Nucl. Med.* 34:7P–8P], potent serotonin transporter ligands, have been radiolabeled with carbon-11 and fluorine-18 as potential radiotracers for localizing and quantifying serotonin transporter sites in the brain using PET. Unfortunately, the in vivo affinity and selectivity for the serotonin transporter of these radiolabeled ligands did not reflect their in vitro potencies as reflected in poor quality images of brain regions rich in serotoninergic neurons. Recently, a series of trans-1,2,3,5,6,10b-hexahydropyrrolo(2,1-a]isoquinoline derivatives, have been found to be potent inhibitors with low and subnanomolar affinity for the serotonin transporter [Maryanoff et al. (1987) *J. Med. Chem.* 30:1433–1454]. The most potent inhibitor of the series, trans-1,2,3,5,6,10b-hexahydro-6-[4-(methylthio)phenyl]pyrrolo[2,1-a]isoquinoline(McN-5652Z)(Ki=0.68 nM), has been labeled with carbon-11 for use as a PET radioligand for mapping serotonin transporter sites [Suehiro et al. (1992) *J. Label Cmpd. Radiopharm.* 31:841–848]. Carbon-11 McN-5652Z showed the greatest accumulation in brain regions rich in serotoninergic neurons with greater cortex to cerebellum ratios (4.3 to 1) than previously tested PET serotonin transporter ligands [Suehiro et al. (1993) *J. Nucl. Med.* 34:120–127. However, the very short 20 minute half-life of carbon-11 is not ideal for longitudinal selective regional uptake of the radioligand and the presence of radiolabeled metabolites that is crucial in binding site imaging and tracer kinetic modeling. Thus, there exists a need for a probe with a longer half-life that demonstrates sub to low nanomolar affinity, high selectivity, and a low dissociation rate from the serotonin transporter binding site. Because the serotonin transporter plays a pivotal role in serotonin neurotransmission, the development of radiopharmaceuticals radiolabeled with gamma or positron emitting isotopes which exhibit pronounced brain uptake, very high selectivity and affinity for the transporter, and low nonspecific binding would be excellent for the measurement of the density of presynaptic serotonin transporter sites by emission tomography.

SUMMARY OF THE INVENTION

The present invention includes compounds of the following general formula:

Formula I where
X is —CH$_2$CH$_2$Q, —CHCHR or —CFCH$_2$ and
Q is F or CH$_2$F, R is I or CH$_2$F,
Y is Y$_1$, except that when Q is CH$_2$F, Y is Y$_2$,
Y$_1$ is H, F, Cl, Br, I and
Y$_2$ is F or Cl.

Any of F, Cl, Br or I may be in stable isotopic or radioisotopic form. Where X is unsaturated, the Z isomer is preferred. Compounds of the invention bind to serotonin transporter with high affinity and selectivity. Radioactivity labeled compounds of the invention labeled with an appropriate isotope are useful as imaging agents for visualizing the location and density of serotonin transporter by PET or SPECT imaging. Certain compounds of the invention can be labeled either with a PET imaging isotope or with a SPECT imaging isotope so that PET and SPECT images using the same tracer compound can be compared and evaluated.

Stable isotopic compounds of the invention have useful pharmacologic properties in the treatment of diseases associated with serotonin transporter dysfunction.

Compounds of the invention vary with respect to the substituents on the phenyl ring. These include, for example:

as well as and the like, where at least one halogen can be radioisotopic. Of particular interest are the radioisotopes $^{18}$F, $^{123}$I, $^{125}$I, $^{131}$I, $^{75}$Br, $^{76}$Br, $^{77}$Br, and $^{82}$Br. For compounds having two halogens, alternative syntheses have been devised to permit rapid substitution of an isotopic halogen at a late step. The same component, for example FEINT, can be synthesized with either $^{123}$I or $^{18}$F, using late step syntheses that permit high radiochemical yield and maximize usable product life.

Also provided are methods for conducting PET and SPECT imaging of a subject with serotonin transporter dysfunction.

DESCRIPTION OF THE DRAWINGS

FIG. 5 shows SPECT images of [$^{123}$I]ZIENT in a rhesus monkey in the transverse (top row), saggital (middle row)

and coronal (bottom row) axes at 15–30 min following i.v. injection of 5 mg Fluvoxamine.

FIG. 6 shows SPECT images of [$^{123}$I]ZIENT in a baboon at 300–360 min i.v. post injection.

DETAILED DESCRIPTION OF THE INVENTION

In general, the terms and phrases used herein have their art-recognized meaning which can be found by reference to standard texts, journal references and contexts known to those skilled in the art. The following definitions are provided to clarify their specific use in the context of the invention.

The term "halogen" refers to both radioactive and non-radioactive isotopes of fluorine, chlorine, bromine, iodine, and astatine. Examples include F, $^{18}$F, $^{19}$F, Cl, $^{35}$Cl, Br, $^{75}$Br, $^{76}$Br, $^{77}$Br, $^{82}$Br, I, $^{123}$I, $^{124}$I, $^{125}$I, $^{131}$I, At, $^{210}$At, and $^{211}$At.

"Z isomer" as used herein refers to a conformation of alkenes in which two substituents with higher atomic numbers on each alkene carbon are on the same side of the double bond. For example, Z isomer of ZIENT refers to the structure which has the phenyl ring and iodine are on the same side of the double bond of phenyl-CH=CHI.

A new series of brain imaging agents in the 4-fluoroalkyl-3-halophenyl nortropane family are described as diagnostic and therapeutic agents for diseases associated with serotonin transporter dysfunction in the present application.

Preferred compounds of the invention exemplified are 2β-carbomethoxy-3β-(4-(2-Z-iodoethenyl-phenyl) nortropane (ZIENT), 2β-carbomethoxy-3-β-(4-(2-fluoroethyl)-3-iodophenyl) nortropane (FEINT) and 2β-carbomethoxy-3β-(4-(2-fluoroethyl)-3-bromophenyl) nortropane (FEBrNT). When labeled with the single photon-emitting radioisotope iodine-123 or the positron-emitting radioisotope fluorine-18, these compounds can be used as a diagnostic imaging agent to measure central nervous system (CNS) neuronal function in the brain of patients suffering from major depression, obsessive compulsive disorder and cocaine addiction. These tropanes were designed to bind with high affinity to the serotonin transporter (SERT). Radiolabeled ZIENT, FEINT and FEBrNT analogs are excellent candidate diagnostic radiopharmaceuticals for differentiating depression from other psychiatric disorders and assisting in the management of treatment of depression. Radiolabeled ZIENT, FEINT and FEBrNT may also be valuable radiopharmaceuticals for assisting in the management of treatment of cocaine addiction.

Figure 1:
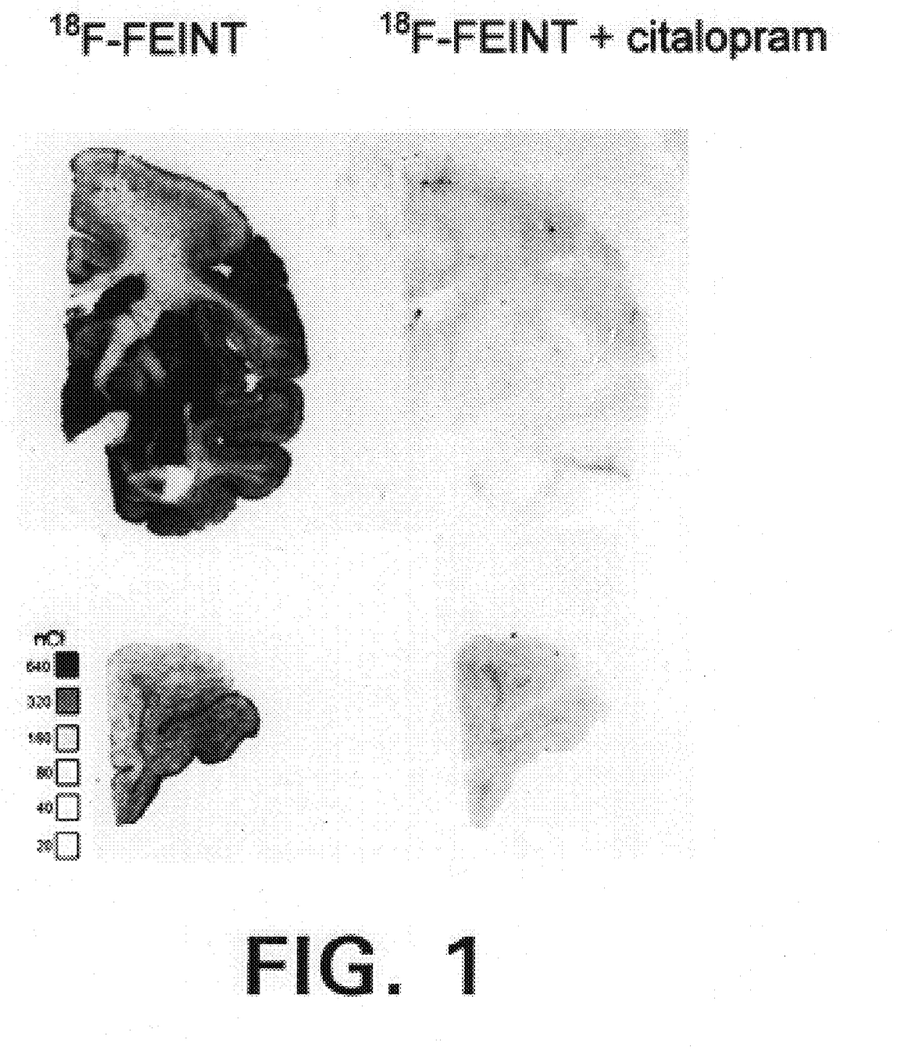
FIG. 1 illustrates regional brain tissue uptake of [$^{18}$F] FEINT (left ha and [$^{18}$F]FEINT with 10 uM Citalopram (right half), indicating specific SERT binding.

Unique characteristics of these radiopharmaceuticals are incorporation of iodine-123 directly on a phenyl ring or as a Z-iodoethenyl group attached to a phenyl group or the attachment of fluorine-18 to a fluoroethyl substituted phenyl ring. These groups were found to be stable to metabolism and in vivo loss of the fluorine-18 and iodine-123 radioisotope. This allows labeling with either fluorine-18 or iodine-123 which gives rise to radiopharmaceuticals that can be used with either positron emission tomography (PET) or single photon emission (SPECT) imaging modalities. In vitro binding studies with FEINT, FEBrNT and ZIENT are shown in Table 1. In cells stably transfected with human SERT using [$^3$H]citalopram afforded Ki (nM) of 0.1, for the dopamine transporter (DAT) in cells stably transfected with human DAT using [$^3$H] WIN35,428 afforded Ki (nM) of 42.4 and for the norepenephrine transporter (NET) in cells stably transfected with human NET using [$^3$H] Nisoxetine afforded Ki (nM) of 64.9 for FEINT. Thus, FEINT was found to be selective and possess a high affinity for SERT with a low affinity for DAT (DAT/SERT=424) and NET (NET/SERT=649). In vitro binding studies with FEBrNT in cells stably transfected with human SERT using [$^3$H] citalopram afforded Ki (nM) of 0.22, for the dopamine transporter (DAT) in cells stably transfected with human DAT using [$^3$H] WIN 35,428 afforded Ki (nM) of 23.2 and for the norepenephrine transporter (NET) in cells stably transfected with human NET using [$^3$H] Nisoxetine afforded Ki (nM) of 126 for FEBrNT. Thus, FEBrNT was found to be selective and possess a high affinity for SERT with a low affinity for DAT (DAT/SERT=100) and NET (NET/SERT= 573). [$^{18}$F]FEINT and [$^{18}$F]FEBrNT were incubated with pig tailed macaque coronal brain slices and the slices apposed to film for 30 min. Binding was localized to the thalamus, hyothalamus, caudate, putamen and temporal cortex. Incubation of the brain slices with [$^{18}$F]FEINT and [$^{18}$F]FEBrNT and 10 uM citalopram maximal inhibition (90%) of binding. A [$^{18}$F]FEINT PET brain imaging study (FIG. 1) in a rhesus monkey demonstrated high [$^{18}$F]FEINT uptake in the thalamus, hypothalamus and brain stem by 105 min post injection. In an equilibrium displacement experiment (FIG. 1) with fluvoxamine (5 mg) in a rhesus monkey, radioactivity in the thalamus, hypothalamus and brain stem were displaced by 55 min post i.v. injection. These results suggest that [$^{18}$F]FEINT and [$^{18}$F]FEBrNT are excellent candidates for in vivo primate studies for mapping SERT sites.

In vitro binding studies with ZIENT in cells stably transfected with human SERT using [$^3$H]citalopram afforded Ki (nM) of 0.031, for the dopamine transporter (DAT) in cells stably transfected with human DAT using [$^3$H] WIN 35,428 afforded Ki (nM) of 3.47 and for the norepenephrine transporter (NET) in cells stably transfected with human NET using [$^3$H] Nisoxetine afforded Ki (nM) of 15 for ZIENT. Thus, ZIENT was found to be selective and possess a high affinity for SERT with a low affinity for DAT (DAT/SERT= 100) and NET (NET/SERT-484). The distribution of radioactivity expressed as percent dose per gram in tissues of unfasted male Sprague Dawley rats at 60 min and 120 min after intravenous administration of [$^{123}$I] ZIENT. [$^{123}$I] ZIENT showed the greatest accumulation in brain regions rich in serotonergic neurons with greater hypothalmus to cerebellum ratios 3 to 1 and 5 to 1 at 60 and 120 min post respectively and prefrontal cortex to cerebellum ratios 2.9 to 1 and 120 min post injection. A [$^{123}$I] ZIENT SPECT brain imaging study in a rhesus money demonstrated high [$^{123}$I] ZIENT uptake in the midbrain by 54 min post injection. In an equilibrium displacement experiment with fluvoxamine (5 mg) in a rhesus monkey, radioactivity in the midbrain was significantly displaced by 35 min post i.v. injection. These data demonstrate that ZIENT labeled with $^{123}$I is a potential radiopharmaceutical for the diagnosis and management of treatment of psychiatric disorders such as depression and obsessive-compulsive disorder in humans using emission tomographic techniques.

Fluorine-18 is the most attractive positron emission tomography PET radionuclide (97% abundant) for radiolabeling because its 110 minute half-life allows sufficient time (3×110 minutes) for incorporation into the radiopharmaceutical and for purification of the final product suitable for human administration. Secondly, fluorine-18 can be prepared in curie quantities as fluoride ion for incorporation into the radiopharmaceutical in high, theoretical 1.7 Ci/nmol, specific activity by no-carrier added nucleophilic subsititution reactions. Fluorine-18 is also the lowest energy positron emitter (0.635 MeV, 2.4 mm positron range) which affords the highest resolution images. Finally the 110 minute half-life allows sufficient time for regional distribution up to a 200 mile radius from the manufacturing site. The only disadvantages to HPI labeled with fluorine-18 is the 110 minute half-life of fluorine-18 which makes regional distribution possible only over a 200 mile radius and the relatively fewer number of PET imaging devices (100) currently available in comparison to 9,000 SPECT systems. These shortcomings can be overcome by labeling with iodine-123. Iodine-123 is the most attractive radioisotope for labeling small molecules for single photon emission tomography (SPECT). Iodine-123 has a 13.13-h half-life with is ideal for regional distribution up to 1,000 miles from the manufacturing site and emits abundant (85) 159 KeV photons which is nearly ideal for currently available 9,000 SPECT systems utilized at all medical centers. Furthermore, radioiodine can be stereospecifically incorporated into radiopharmacueticals in high specific activity and high yield by kit methodology.

The serotonin and norepinephrine transporters have been convincingly implicated in the pathophysiology of major depression and represent the putative sites of action of the majority of the older and newer generation antidepressants [Murphy et al. (1986) supra]. Supporting evidence has, however, been indirect resulting from the study of postmortem tissue and animal and peripheral cell models of transporter cell function and pharmacology. Emission tomography techniques present unique opportunities to define the functional status and pharmacology in the living human brain. The development of serotonin transporter (SERT) imaging agents labeled with positron and gamma emitting radionuclides [Suehiro et al. (1993) supra] has been of recent interest as probes to study the roles of this neuroregulatory site using positron emission tomography (PET) and single-photon emission tomography (SPECT).

Recently, it was reported that replacement of the 3β-(4-iodophenyl) group of 2β-carbomethoxy-3β-(4-iodophenyl) nortropane (nor-CIT) with a 3β-(4-ethyl-3-iodophenyl) group afforded the analog (EINT) which was found to show subnanomolar affinity for the SERT ($IC_{50}$=0.69 nM vs [$^3$H]WIN 35428) and to be 500 times more selective for the SERT than the dopamine transporter (DAT) ($IC_{50}$=329 nM vs [$^3$H]paroxetine) [Blough B. E., et al. (1997) *J. Med. Chem.* 40:3861]. This suggested to us that the 3β-4' ethylphenyl substituent could allow introduction of sulfonyl esters for incorporationg fluorine-18 as 4'-[$^{18}$F] fluoroethyl group. Therefore, several new radioligand bioisosteres of EINT: 2β-carbomethoxy-3β-(4-(2-fluoroethyl)-3-iodophenyl)nortropane (FEINT, 10a), 2β-carbomethoxy-3β-(4-3-fluoropropyl)-3-iodophenyl)nortropane (FPINT, 10b) and 2β-carbomethoxy-3β-(4-(2-fluoroethyl)-3-bropmophenyl)nortropane (FEBrNT, 12) were synthesized as potential PET and SPECT SERT imaging agents that could be labeled with either fluorine-18, bromine 75, 76, carbon 11 or iodine-123.

Scheme 1 provides exemplary synthetic routes for the preferred compounds of the invention, e.g. FEINT, FPINT and FEBrNT. Modification of the materials and methods can be made by routine choice and without undue experimentation by those skilled in the art. The preparation of analogues 10a,b involved a seven step sequence of reactions. In this synthetic approach methyl anhydroecgonine was treated with a 4-trimethylsilylphenylmagnesium bromide to give the corresponding 2β-carbomethoxy-3β-(4-trimethylsilyphenyl)tropane (2). The tropane 2 was treated with bromine monochloride followed by vinyltribytyltin and allyltributyltin tro afford 4a and 4b respectively. Tropanes 4a and 4b were converted to their corresponding ω-alcohols followed by reaction with $I_2$ to give 3β-4'-(ω-acetoxylalkyl)-3'-iodophenyltropanes 6a and b. Tropanes 6a and 6b were treated with TrocCl/HCl MeOH followed by DAST and Zn to form the corresponding nortropanes FEINT (10a) and FPINT (10b). FEBrNT (12b) was prepared in a five-step reaction sequence from 6a by conversion to 3β-4'-(2-acetoxyethyl)-3'-bromophenyltropane followed by desmethylation and fluorination as described for 10a.

Scheme 1

-continued a. p-BrMgC₆H₄SiMe₃ b. NCS/KBr c. Bu₃SnCH=CH₂ or Bu₃SnCH₂CH=CH₂/Pd(Ph₃P)₄ d. 1. BH(c-C₁₆H₁₁)₂ 2. H₂O₂
e. I₂/HgO/HClO₄ f. 1. TrocCl 2. HCl/MeOH g. 1. TsCl/Et₃N 2. Zn/CH₃COOH h. (Boc)₂O i.1. K[¹⁸F]F/K222 2. TFA
j. 1. DAST 2. Zn/CH₃COOH The results of binding site competition studies using cell lines stably expressing the human DAT, SERT and NET and using [$^3$H]WIN 35428 for DAT sites, [$^3$H]nisoxetine for NET are shown in Table 1. The rank order of affinity for binding to human SERT was FEINT=Nor-CIT>FEBrNT= FPINT=fluvoxamine. These results demonstrated that FEINT, FPINT and FEBrNT had subnanomolar SERT affinity. FEINT and FEBrNT were the only selective ligands for SERT when compared to both DAT and NET binding sites (Table 1). FEINT and FEBrNT have a very high affinity (0.12–0.24 nM) for SERT and 283 and 100 times higher selectivity for SERT over DAT respectively. Radio synthetic methods for [$^{18}$F]FEINT, [$^{18}$F]10a and [$^{18}$F]FEBrNT, [$^{18}$F] 12 were developed for in vitro autoradiographic analysis in rhesus monkey brain slices and in vivo evaluation in rats and non-human primates.

The radiosynthesis for [$^{18}$F]10a and [$^{18}$F]12 employed the tosylates 9a and 13 as the substrates respectively. The tosylate 9a was treated with NCA K[$^{18}$F]/K222 for 10 min in 1 mL of $CH_3CN$ at 85° C. followed by $TFA/CH_2Cl_2$ at 27° C. HPLC purification on a Waters $C_{18}$ RP 25 mm×100 mm, 80:20:0.1 $CH_3OH:H_2O:NEt_3$, flow rate 6 mL/min, afforded [$^{18}$F]FEINT in 8% radiochemical yield E.O.B. in a total synthesis time of 150 min. [$^{18}$F]FEBrNT was synthesized from the tosylate 13 in a similar manner. [$^{18}$F]FEINT and [$^{18}$F]FEBrNT were incubated with pig tailed macaque coronal brain slices. Binding of [$^{18}$F]FEINT and [$^{18}$F]FEBrNT were localized to the thalamus, hypothalamus, caudate, amygloid complex, putamen and temporal cortex. Incubation of the brain slices with 10 uM citalopram resulted in maximal inhibition (90%) of binding.

Further provided by this invention is a kit for the rapid synthesis of the compounds of Formula I. The kid includes a compound of the formula below (Formula II) capable of reacting with a reagent capable of displacing L and replacing L with a substituent containing a radioactive group.

Formula II

L is a leaving group, as understood by those of ordinary skill in the art, and can be displaced by a substituent containing a radioactive halogen. Preferred radioactive halogens include $^{18}$F, $^{123}$I, $^{125}$I, $^{131}$I, $^{75}$Br, $^{76}$Br, $^{77}$Br, and $^{82}$Br. Y is selected from the group consisting of H, F, Cl, Br, and I. The compounds made by this kit can be used for diagnostics and imaging and hence preferably contain a radioactive isotope of a halogen.

The long-lived isotopes, such as $^{123}$I with a half-life of 13 hours, are commercially available from sources such as Nordion International Ltd. ((Vancouver, B.C., Canada) or NEN/DuPont (N. Billerica, Mass.). Shorter-lived isotopes, such as $^{18}$F can be obtained from a regional source, with a ~200 mile radius of the site of intended use.

The described kit is intended for use with a reagent capable of displacing L and replacing L with a substituent containing a radioactive group.

Optionally, the kit can include items of apparatus, such as a reaction vessel, device for transferring isotopic material to the reaction vessel, pre-packed separation column for separating product from excess reactants, shielding and the like, as known in the art. See, e.g. Zea-Ponce, U., et al (1998) *J. Nuclear Med.* 36:525–529.

An initial ex vivo autoradiographic study was performed with either [$^{18}$F]FEINT or [$^{18}$F]FEBrNT in rats to measure brain penetration and regional distribution. A male Sprague Dawley rat was injected with one mCi of no-carrier added [$^{18}$F]FEINT or [$^{18}$F]FEBrNT. A second rat was injected with 5 mg/kg of fluvoxamine 20 min prior to tracer injection. Binding was localized to the thalamus, hypothalamus, caudate, putamen and amygloid complex. Blocking with fluvoxamine resulted in maximal inhibition of binding. These results suggest that [$^{18}$F]FEINT and [$^{18}$F]FEBrNT were excellent candidate SERT imaging agents for further evaluation in rats in vivo by regional tissue distribution studies.

The in vivo regional brain tissue distribution of [$^{18}$F] FEBrNT (Table 2) and [$^{18}$F]FEINT Tables 3 and 4) were compared with a preliminary study in rats. [$^{18}$F]FEBrNT showed higher uptake, 1.2% dose/g, than [$^{18}$F]FEINT (0.5% dose/g) Table 3) in the SERT rich hypothalamus at 60 min post injection. [$^{18}$F]FEBrNT also exhibited higher hypothalamus to cerebellum ratios. The hypothalamus to cerebellum ratios for [$^{18}$F]FEBrNT were 5.7 at 60 min post injection in comparison to 4.8 for [$^{18}$F]FEINT. The regional brain tissue uptake and clearance of [$^{18}$F]FEINT was studied in male Sprague Dawley Rats over 2 h. The results shown in Table 4 demonstrate that [$^{18}$F]FEINT showed rapid washout from the hypothalamus with 75% and 85% clearance at 60 and 120 min, respectively when compared to 5 min post injection. Low uptake and rapid clearance of [$^{18}$F]FEINT resulted in low hypothalamus and striatum to cerebellum ratios, 2.8 and 1.7 respectively at 120 min post injection. These preliminary results indicated that [$^{18}$F]FEBrNT was the better candidate for imaging the SERT in non-human primates by PET. The regional distribution of [$^{18}$F]FEBrNT and [$^{18}$F]FEINT were next studied in the brain of rhesus monkeys.

Figure 2:
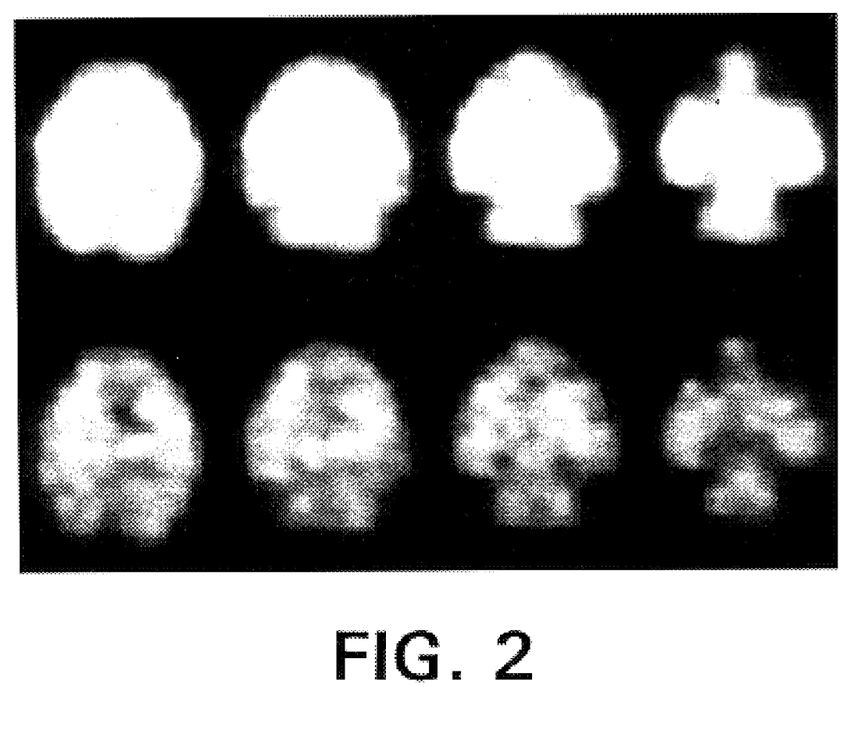
FIG. 2 (top row) shows PET images of [$^{18}$F]FEBrNT in a Rhesus Money at 100–120 min i.v. post injection; and (bottom row) 45–50 min following i.v. of 5 mg Fluvoxamine indicating specific SERT binding.
Figure 3:
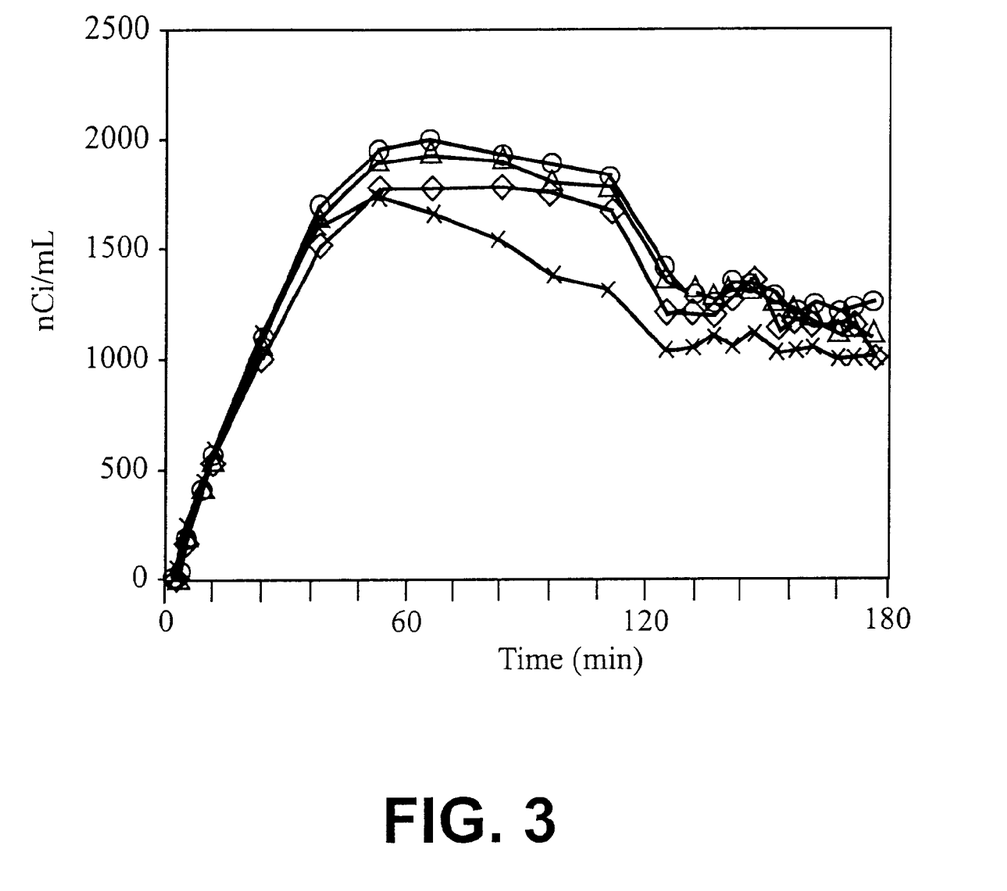
FIG. 3 is a graph showing time activity curves of [$^{18}$F] FEBrNT in a rhesus monkey in the thalamus (○), hypothalamus (Δ), pons (◇) and cerebellum (x) at 0–120 min i.v. post injection. At 112 min post injection, 5 mg of Fluvoxamine was administered.

The regional uptake of [$^{18}$F]FEBrNT in the brain of an anesthetized rhesus monkey is shown in FIGS. 2 and 3. Only [$^{18}$F]FEBrNT exhibited high uptake and retention in the thalamus, hypothalamus and pons. Images of the rhesus brain following administration of [$^{18}$F]FEINT showed no visible uptake of radioactivity in the midbrain and brain stem. The peak uptake ratio of [($^8$F]FEBrNT by fluvoxamine (5 mg) was performed to determine whether midbrain (thalamus/hypothalaus) radioactivity reflected binding to SERT affinity sites. The results of the displacement study, shown in FIGS. 2 and 3, clearly demonstrate that fluvoxamine, an SSRI, significantly displaced the uptake of [$^{18}$F]FEBrNT from the SERT transporter rich thalamus, hypothalamus and pons.

In summary, a series of 2β-carbomethoxy-3β-(4-fluoroalkyl-3-halophenyl)-nortropanes as potential SERT PET imaging agents were synthesized and evaluated for the monoamine transporter affinity using in vitro competitive binding. These studies demonstrated that only analogues FEINT and FEBrNT exhibited very high affinity and selectivity for SERT. Fluorine-18 labeled FEINT and FEBrNT were prepared in a 2-step reaction sequence and in 8% RCY. In vitro autoradiograms of both [$^{18}$F]FEINT and [$^{18}$F] FEBrNt exhibited high density labeling for thalamus, hypothalamus, caudate, amygloid complex and putamen. In in vivo tissue distribution in rats and PET imaging in rhesus monkeys, only [$^{18}$F]FEBrNT demonstrated specific binding to mid brain regions rich in SERT sites. These studies indicate that fluorine-18 labeled FEBrNT is an excellent candidate for further study as an in vivo imaging agent to quantitate SERT binding sites by PET.

Studies by Blough, et al., [Bough, et al. (1996) *J. Med. Chem.* 39(20):4027–35] indicated that introduction of isopropenyl and cis-propenyl substituents at the 4'-position of the 3β-phenyl ring afforded the analogs with affinity and specificity for SERT. 2β-carbomethoxy-3β-(4'-isopropenylphenyl)nortropane (nor-β-CIPPT) and 2β-carbomethoxy-3β-(4'cis-propenylphenyl)notropane (nor-β-CCPPT) were found to be the most potent alkenyl analogs. Nor-β-CIPPT showed subnanomolar affinity for the SERT ($IC_{50}$=0.6 nM vs [$^3$H]paroxetine) and to be 38 times more selective for the SERT than the dopamine transporter (DAT)($IC_{50}$=23 nM vs [$^3$H]WIN 35428). Nor-β-CCPPT possessed lower affinity for the SERT ($IC_{50}$=1.15 nM vs [$^3$H]paroxetine) and was found to be 28 times more selective for the SERT than the dopamine transporter (DAT)($IC_{50}$=32 nM vs [$^3$H]WIN 35428). These studies strongly suggest that the incorporation of fluorine and iodine at a 4'-isopropene, cis-propene and vinyl substituent at the 4'-position of the 3β-phenyl ring can lead to a potent SERT ligand. Thus, several new halogen bioisosteres of nor-β-CIPPT and nor-β-CCPPT, e.g. 2β-carbomethoxy-3β-4'-(Z-2-iodoethenyl)phenyl)nortropane (ZIENT), 2βcarbomethoxy-3β-(4'(Z-3-fluoropropenyl)phenyl)-nortropane (ZFPPNT) and 2β-carbomethoxy-3β-4'-(2-fluoroisopropenyl)phenyl)nortropane (FIPPNT) were synthesized, as potential PET and SPECT SERT imaging agents that could be labeled with either fluorine-18, carbon-11 or iodine-123.

Schemes 2–4 provide exemplary synthetic routes for the preferred compounds of the invention, e.g. ZEINT, ZFPPNT and FIPPNT. The preparation of ZIENT involved a five-step sequence of reactions (Scheme 2). In this synthetic approach 2β-carbomethoxy-3β-4('-bromophenyl)nortropane was treated with vinyltribytyltin to 2β-carbomethoxy -3β-(4'-5ethenylphenyl)nortropane. The N-Boc vinylnortropane derivative was converted to the N-Boc 2β-carbomethoxy-3β-4'-formylphenyl)nortropane followed by reaction with triphenyl-phosphoniumiodomethyne yllide and removal of the N-Boc group to give ZIENT.

Scheme 2 a. $Bu_3SnCH=CH_2/Pd(Ph_3P)_4$ b. $(Boc)_2O$ c. $OsO_4$, $NaIO_4$ d. $(Ph_3P)CH_2I_2$, $((CH_3)_3Si)_2NH$ e. HCl/MeOH
f. $Me_3SnSnMe_3$, $Pd(Ph_3P)_4$ g. $Na[^{123}I]I$, $H_2O_2$.

ZFPPNT was synthesized by the six step reaction sequence outlined in Scheme 3. In this synthetic approach N-Troc CIT was treated with propargyl alcohol to give N-Troc-2β-carbomethoxy-3β-4'-(3-hydroxypropynyl)phenyl)nortropane. The N-Troc hydroxypropargyl-nortropoane derivative was reacted with DAST to afford N-Troc-2β-carbomethoxy-3β-4'-3-fluoropropynyl)phenyl)nortropane. Removal of the Troc followed by reduction of the alkyne with a hydrogen, quinoline and a Lindlar catalyst yielded ZFPPNT.

Scheme 3 a. ICI b. TrocCl c. CuI HCCCH₂OH/PdCl₂(Ph₃P)₂, DiPA d. DAST e. Zn, HOAc f. H₂/PdC, BaSO₄, Quinoline Scheme 4

FIPPNT a. CuI HCCSi(CH₃)₃/PhCl₂(Ph₃P)₂, DiPA  b. (nBu)₄NF  c. HgSO₄, MeOH  d. Ph₄CH₃I, nBuLi
e. PhSeBr, H₂O₂  f. 1. (nBu)₄NF  2. Zn, HOAc

FIPPNT was synthesized by the six step reaction sequence outlined in Scheme 4. In this synthetic approach N-Troc CIT was treated with trimethylsilylacetylene to give N-Troc-2β-carbomethoxy-3β-(4'-(3-trimekthylsilylethy-nyl)phenyl)nortropane. The N-Troc trimethysilyl-ethynyl-nortropane derivative was reacted with fluoride and mercuric sulfate to afford N-Troc 2β-carbomethoxy-3β-(4'-acetophenyl)nortropane. The pivotal step of the synthesis involved conversion of the methyl ketone to the corresponding 3β-(4'-(2-bromoisopropenyl)nortropane. Removal of the Troc yielded FIPPNT.

The results of binding site competition studies using cell lines stably expressing the human DAT, SERT and NET and using [³F]WIN 35428 for DAT sites, [³F]nisoxetine for NET are shown in Table 1. The rank order of affinity for binding to human SERT was ZIENT>FIPPNT>ZFPPNT>fluvoxamine>EIENT. These results demonstrated that ZIENT, FIPPNT and FIPPNT had subnanomolar SERT affinity. ZIENT, FIPPNT and FIPPNT were also highly selective ligands for SERT when compared to both DAT and NET binding sites (Table 5). ZIENT, FIPPNT and ZFPPNT had a very high affinity 0.03–0.1 nM binding affinity for SERT and 116, 37 and 116 times higher selectivity for SERT over DAT respectively. These results strongly indicate that ZIENT, FIPPNT and ZFPPNT are excellent candidates for further studies to evaluate their potential as SERT imaging agents. A radiosynthetic method for [¹²³I]ZIENT, was developed for in vivo evaluation in rats and non-human primates.

A radiosynthetic method for [¹²³I]ZIENT was developed to evaluate its regional in vivo brain distribution. This radiosynthesis employed a trimethytltin substrate (Scheme 2). The tin precursor was treated with 14.5 mCi NCA [¹²³I]NaI and 3% H₂O₂ in ethanolic HCl. HPLC purification on a Waters C₁₈ RP 8 mm, 80:20:0.1 CH₃OH:H₂O:NEt₃, flow rate 1 mL/min afforded 8.5 mCi [¹²³I]ZIENT, 69% radiochemical yield E.O.B. in a total synthesis time of 360 min with a specific activity of 1700 mCi/μmol.

The in vivo regional brain tissue distribution of [¹²³I]ZIENT (Table 7) was evaluated in a preliminary study in rats. [¹²³I]ZIENT showed high uptake, 0.7% dose/g in the SERT rich hypothalamus at 60 min post injection. [¹²³I]ZIENT, showed a slow washout from the hypothalamus with only 30% clearance at 120 min when compared to 60 min post injection. The hypothalamus to cerebellum ratios for [¹²³I]ZIENT were 2.7 at 60 min post injection and increased to 4.4 at 120 min post injection. To determine the in vivo specificity of [¹²³I]ZIENT for rat brain SERT, a study was performed in which unlabeled monoamine transporter specific ligands (5 mg of ligand per kg body weight of rat) were intravenously administered 15 min prior to the intravenous administration of [¹²³I]ZIENT. The monoamine transporter ligands administered were GBR-12909 (DAT), fluvoxamine (SERT) and reboxetine (NET). The rats were sacrificed 60 min after injection of [¹²³I]ZIENT and the hypothalamus, striatum, prefontal cortex, and cerebellum were dissected and the uptake of radioactivity determined. The results of this study, shown in Table 7 clearly demonstrate that fluvoxamine, the SERT ligand, significantly blocked the uptake of [¹²³I]ZIENT in the SERT transporter rich hypothalamus and stratum. GBR 12909, the DAT ligand, did not significantly block the uptake of [¹²³I]ZIENT in the striatum indicating that uptake of radioactivity in striatum was primarily associated with SERT binding. The NET blocking agent showed little effect on the regional brain uptake of [¹²³I]ZIENT. These preliminary data strongly indicate that [¹²³I]ZIENT is an excellent candidate SERT radioligand for SPECT.

Figure 4:
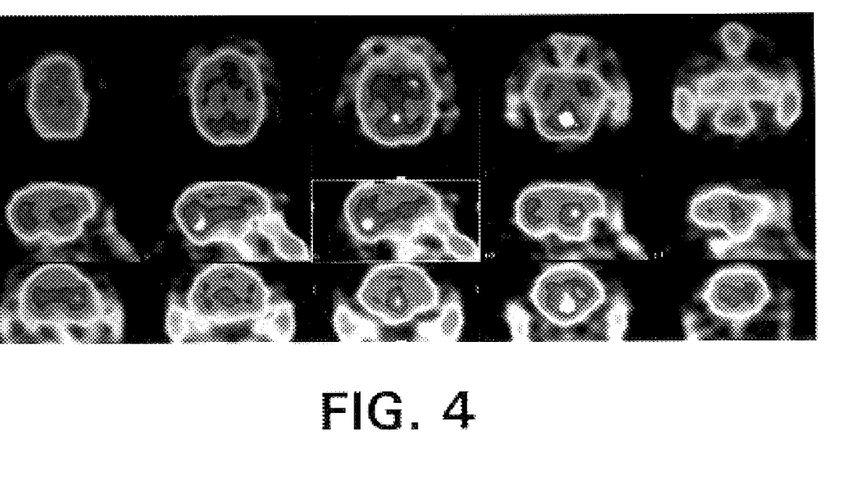
FIG. 4 shows SPECT images of [$^{123}$I]ZIENT in a rhesus monkey at 80–110 min i.v. post injection in the transverse (top row), saggital (middle row) and coronal axes (bottom row).

We performed preliminary dynamic brain SPECT imaging studies using an ADAC Vertex dual-headed gamma camera and [¹²³I]ZIENT in a rhesus monkey and using an CERASPECT camera (Collaborators J. Staley and R. Innis, West Haven, Va. Medical Center) in a baboon. The rhesus monkey was injected with 6.27 mCi and planar images were collected to measure initial brain uptake (2 minute acquisitions from 0 min to 20 min after injection) followed by serial images (12-minute acquisitions from 20 min to 110 min after injection). SPECT images were reconstructed as transaxial slices (3.2 mm) and attenuation corrected. The superior and inferior brainstem were regions of highest uptake in the brain and showed clear visualization at 80–110 min after injection (FIG. 4).

Figure 5:
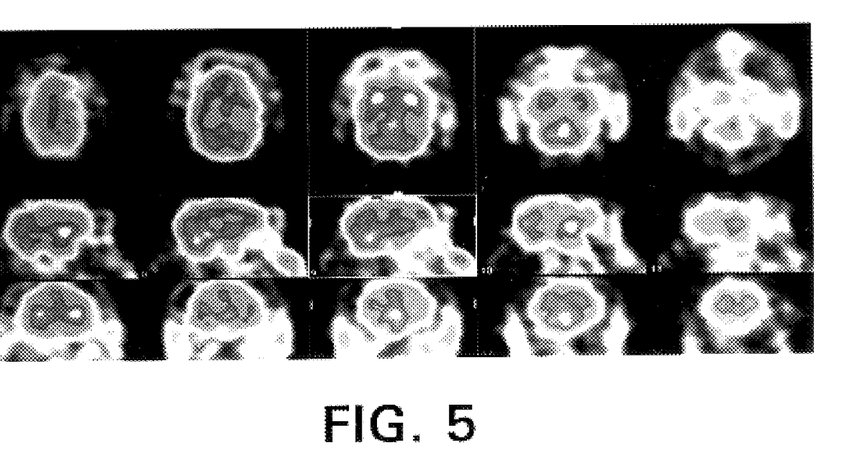

A chase study with [¹²³I]ZIENT and fluvoxamine, a selective serotonin transporter inhibitor, was also performed in the same rhesus monkey (FIG. 5). At 110 min 5.0 mg of fluvoxamine was administered intravenously and dynamic transaxial SPECT imaging was continued for an additional thirty minutes. After 30 min following administration of fluvoxamine the SPECT images clearly showed a significant reduction of activity in the superior and inferior brainstem. These results indicate that [$^{123}$I]ZIENT is binding to SERT sites.

Figure 6A:
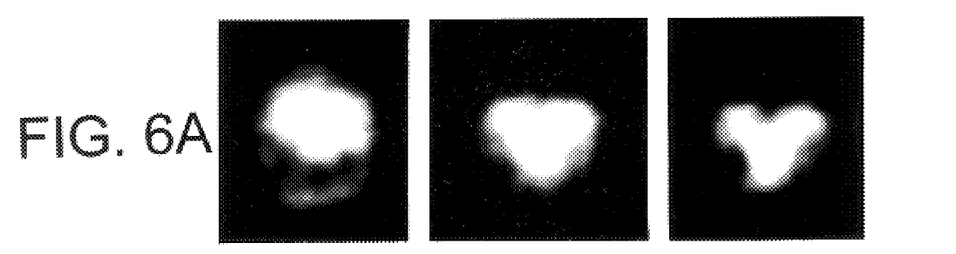
FIG. 6A is the transverse axis.
Figure 6B:
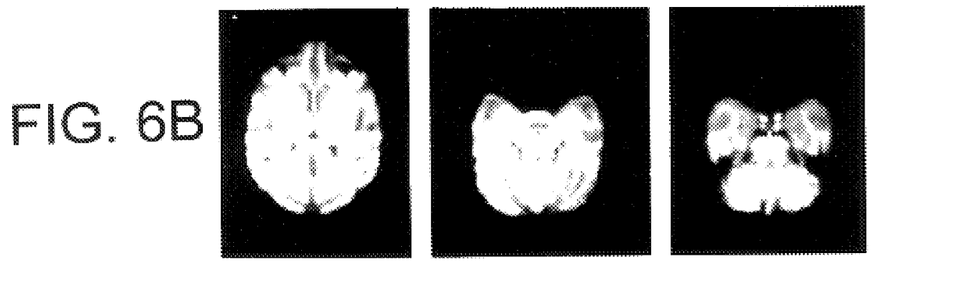
FIG. 6B is MRI co-registration.
Figure 7:
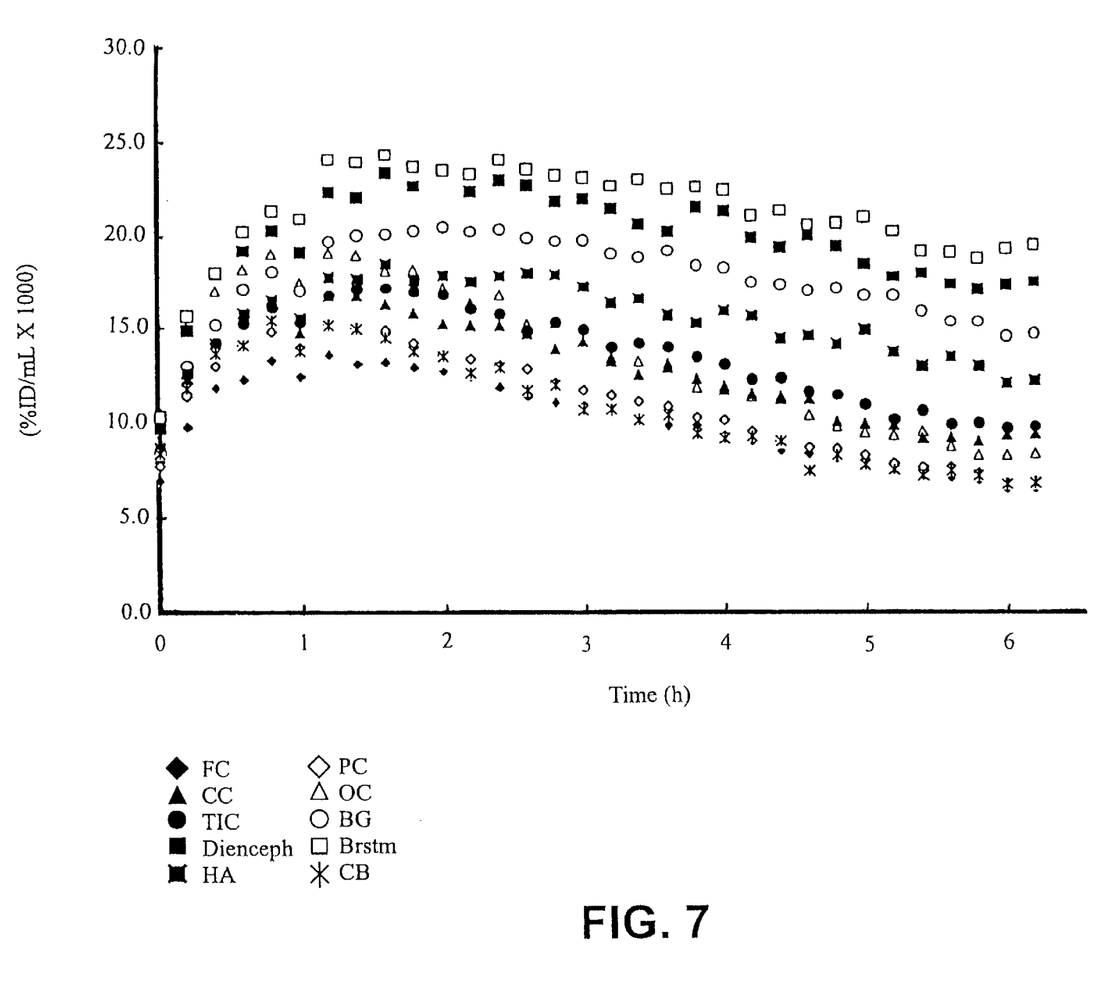
FIG. 7 is a graph showing time activity curves of [$^{123}$I] ZIENT in a baboon.

SPECT data acquired with the CERASPECT camera had a resolution in all three axes of approximately 12 mm full width half-maximum measured using a $^{123}$I line source and 20 cm water-filled cylindrical phantom that was reconstructed using a cutoff of 1 cm. The baboon was injected with 10 mCi of [$^{123}$I]ZIENT and serial images (128×128×64 matrix: pixel size=1.67×1.67 mm, slice, thickness=1.67 mm, voxel volume=4.66 mm$^3$) were acquired at 159 1.67×1.67 mm, slice thickness=1.67 nm, voxel volume=4.66 mm$^3$) were acquired at 159 keV, in step and shoot mode at 10 min each for a total of 360 to 390 min and 32 to 35 acquisitions per experiment. Images were reconstructed using a ramp and a Butterworth filter (cutoff=0.65 cm−power factor=10). To identify brain regions, MRI scans of 1.5 mm contiguous slices were obtained with a 1.5 Tesla GE Signa device. Axial images were acquired using a spoiled GRASS (gradiant recall acquisition in the steady state) sequence with TR=25 ms, TE=5 ms, NEX=2, matrix=256×192, field of view=16 cm. The diencepalon, superior and inferior brainstem and striatum were the regions of highest uptake in the brain and showed clear visualization at 300–360 min after injection (FIG. 6). The regional uptake of [$^{123}$I]ZIENT in the brain of an anesthetized baboon is shown in FIG. 7. The uptake ratio of brainstem/cerebellum was 3.0:1 at 300–360 min.

In summary, ZIENT is the first reported 3β-aryl nortropane serotonin transporter imaging agent labeled with iodine-123 that exhibits specific in vivo SERT binding. Preliminary in vivo pharmacokinetic studies in rats and imaging studies in a rhesus monkey and a baboon with iodine-123 labeled ZIENT show high brainstem uptake with high brainstem to cerebellum ratios. A chase study with the SSRI fluvoxamine demonstrates that ZIENT is specific for CNS SERT.

Based on these studies, the present invention provides a method for conducting positron emission tomography or single photon emission tomography of a subject comprising: (1) administering to the subjectr an image-generating amount of a compound of Formula I which contains at least one radioactive halogen; and (2) measuring the distribution within the subject of the compound by PET or SPECT.

TABLE 1

Relative transporter affinity of candidate Tropane SERT ligand in transfected cell lines

| Ligand | X | Y | DAT[1], Ki (nM) | NET[2], Ki (nM) | 5-HTT[3], Ki (nM) |
|---|---|---|---|---|---|
| FEINT | FCH$_2$CH$_2$ | I | 34*, 42.4$^\Psi$ | 64.9$^\Psi$ | 0.12*, 0.65$^\#$, 0.1$^\Psi$ |
| FPINT | FCH$_2$CH$_2$CH$_2$ | I | 0.016* | — | 0.26* |
| FEBrNT | FCH$_2$CH$_2$ | Br | 24.6$^\wedge$, 23.2$^\Psi$ | 97$^\wedge$, 126$^\Psi$ | 0.24*, 0.075$^\wedge$, 0.22$^\Psi$ |
| Z-IENT | ICH=CH | H | 3.47$^\wedge$ | 15$^\wedge$ | 0.06*, 0.031$^\wedge$ |
| E-IENT | ICH=CH | H | 1.88* | — | 1.15$^\#$ |
| Z-3-FPNT | FCH$_2$CH=CH | H | 11.6* | — | 0.1*, 0.59$^\#$ |
| FECNT | | | 0.22*, 0.2$^\Psi$ | 610$^\Psi$ | 23$^\Psi$ |
| Nor-CIT | | | | | 0.12* |
| GBR 12909 | | | 0.6$^\wedge$, 041$^\Psi$ | — | — |
| Desipramine | | | — | 0.49$^\wedge$, 0.34$^\Psi$ | |
| Fluvoxamine | | | — | — | 0.71$^\wedge$, 0.24*, 2.25$^\#$ 1.46$^\Psi$ |

[1][$^3$H]WIN 35428 as reference for dopamine transporter site.
[2][$^3$H]Nisoxetine for norepinephrine transporter site.
[2][$^3$H]Citalopram for serotonin transporter site.
4. *, #, ^, $\Psi$ results from the same binding study

TABLE 2

Regional Uptake (% Dose/g) of Radioactivity in Brains of Unfasted Male Sprague Dawley Rats (n = 3–4) 60 min following Intravenous Administration of [$^{18}$F]FEBrNT (12)

| Region | No Block | Fluvoxamine | RTI-113 | Reboxetine |
|---|---|---|---|---|
| Striatum | 0.45 | 0.29 | 0.45 | 0.36 |
| | (0.28–0.61) | (0.26–0.31) | (0.40–0.50) | (0.35–0.62) |
| Frontal Cortex | 0.29 | 0.26 | 0.32 | 0.28 |
| | (0.23–0.34) | (0.20–0.33) | (0.27–0.36) | (0.26–0.43) |
| Cerebellum | 0.21 | 0.19 | 0.23 | 0.19 |
| (CB) | (0.15–0.28) | (0.16–0.22) | (.16–.30) | (0.17–0.20) |
| Hypothalamus | 1.2 | 0.83 | 1.3 | 1.07 |
| | (0.96–1.5) | (0.71–0.84) | (1.2–1.34) | (0.94–1.26) |
| Brain | 0.26 | 0.19 | 0.26 | 0.23 |
| | (0.21–0.32) | (0.16–0.23) | (0.22–0.30) | (0.20–0.26) |
| Hypothal/(CB) | 5.7 | 4.36 | 5.7 | 5.6 |
| Striatum/(CB) | 2.1 | 1.5 | 2.0 | 1.9 |

TABLE 3

Tissue uptake of Radioactivity in Unfasted Male Sprague Dawley Rats (n = 3–4) 60 min following Intravenous Administration of [$^{18}$F]FEINT (10a)

| Region | No block | Fluvoxamine |
|---|---|---|
| Blood | 0.09 (0.09–0.99) | 0.07 (0.06–0.08) |
| Olf. T. | 1.46 (1.24–1.65) | 0.04 (0.19–0.55) |
| Prefrontal Cortex | 0.25 (0.21–0.29) | 0.18 (0.06–0.41) |
| Striatum | 0.25 (0.21–0.29) | 0.2 (0.16–1.40) |
| Hypothalamus | 0.5 (0.32–0.77) | 0.38 (0.28–0.45) |
| Cortex | 0.18 (0.15–0.19) | 0.15 (0.15–0.73) |
| Cerebellum | 0.11 (0.11–0.12) | 0.1 (0.09–0.12) |
| Hypothal/(CB) | 4.6 | 3.8 |
| Striatum/(CB) | 2.3 | 2.0 |

TABLE 4

Tissue uptake of Radioactivity in Unfasted Male Sprague Dawley Rats (n = 3–4) following Intravenous Administration of [$^{18}$F]FEINT (10)

| Tissue | 5 min | 30 min | 60 min | 120 min |
|---|---|---|---|---|
| Blood | 0.19 | 0.14 | 0.10 | 0.63 |
|  | (0.15–0.23) | (0.13–0.15) | (0.08–0.11) | (0.58–0.68) |
| Pre-frontal | 0.75 | 0.37 | 0.14 | 0.10 |
| Cortex | (0.54–0.87) | (0.33–0.42) | (0.11–0.19) | (0.09–0.11) |
| Striatum | 0.84 | 0.39 | 0.22 | 0.10 |
|  | (0.59–1.20) | (0.29–0.55) | (0.17–0.31) | (0.09–0.13) |
| Hypothalamus | 0.97 | 0.66 | 0.24 | 0.17 |
|  | (0.58–1.59) | (0.51–0.89) | (0.18–0.30) | (0.26–0.17) |
| Cortex | 0.76 | 0.36 | 0.13 | 0.09 |
|  | (0.64–0.96) | (0.34–0.40) | (0.10–0.17) | (0.08–0.11) |
| Cerebellum | 0.58 | 0.23 | 0.09 | 0.06 |
|  | (0.51–0.65) | (0.22–0.23) | (0.07–0.11) | (0.05–0.08) |
| Bone | 0.27 | 0.70 | 0.95 | 1.26 |
|  | (0.23–0.31) | (0.36–0.92) | (0.53–1.17) | (0.94–1.67) |
| Brain | 0.65 | 0.35 | 0.14 | 0.89 |
|  | (0.56–0.75) | (0.32–0.40) | (0.12–0.18) | (0.08–0.11) |
| Hypothal/(CB) | 1.67 | 2.87 | 2.67 | 2.83 |
| Striatum/(CB) | 1.45 | 1.70 | 2.44 | 1.67 |

TABLE 5

Relative transporter affinity of candidate SERT ligands in transfected cell lines

| Ligand | DAT[1], Ki (nM) | NET[2], Ki (nM) | 5-HTT[3], Ki (nM) |
|---|---|---|---|
| ZIENT | 3.47 | 15 | 0.03 |
| EIENT | 1.88 | — | 1.15 |
| ZFPPNT | 11.6 | — | 0.1 |
| FIPPNT | 2.93 | 11.84 | 0.08 |
| GBR 12909 | 0.6 | — | — |
| Desipramine | — | 0.49 | — |
| Fluvoxamine | — | — | 0.71 |

[1][$^3$H]WIN 35428 as reference for dopamine transporter site.
[2][$^3$H]Nisoxetine for norepinephrine transporter site.
[3][$^3$H]Citalopram for serotonin transporter site.

TABLE 6

Tissue uptake of Radioactivity in Unfasted Male Sprague Dawley Rats (n = 3–4) Intravenous Administration of [$^{123}$I]ZIENT

| Tissue | 5 min | 30 min | 60 min | 120 min |
|---|---|---|---|---|
| Blood | 0.64 | 0.46 | 0.39 | 0.33 |
|  | (0.52–0.86) | (0.43–0.49) | (0.23–0.42) | (0.31–0.36) |
| Heart | 2.41 | 0.52 | 0.36 | 0.20 |
|  | (2.36–2.47) | (0.48–0.55) | (0.15–0.40) | (0.18–0.24) |
| Lung | 9.71 | 1.48 | 1.27 | 0.72 |
|  | (7.9–11.8) | (1.35–1.66) | (0.62–1.44) | (0.61–0.78) |
| Liver | 0.99 | 0.43 | 0.28 | 0.29 |
|  | (0.73–1.33) | (0.38–0.51) | (0.11–0.30) | (0.23–0.41) |
| Spleen | 3.79 | 1.24 | 0.82 | 0.51 |
|  | (3.28–4.67) | (1.03–1.50) | (0.50–0.94) | (0.44–0.55) |
| Kidney | 2.35 | 0.66 | 0.44 | 0.32 |
|  | (2.16–2.67) | (0.64–0.70) | (0.29–0.50) | (0.29–0.35) |
| Thyroid | 0.11 | 0.23 | 0.33 | 1.61 |
|  | (0.08–0.12) | (0.19–0.29) | (0.17–0.37) | (0.82–2.31) |
| Muscle | 0.30 | 0.29 | 0.20 | 0.16 |
|  | (0.15–0.44) | (0.25–0.32) | (0.11–0.22) | (0.14–0.18) |
| Testis | 0.22 | 0.36 | 0.29 | 0.30 |
|  | (0.19–0.27) | (0.30–0.47) | (0.26–0.34) | (0.26–0.33) |

TABLE 7

Regional uptake of Radioactivity in Brains of Unfasted Male Sprague Dawley Rats (n = 3–4) following Intravenous Administration of [$^{123}$I]ZIENT (6e)

| Region | 60 min | Fluvoxamine | GBR 12909 | 120 min |
|---|---|---|---|---|
| Striatum | 0.60 | 0.28 | 0.40 | 0.46 |
|  | (0.54–0.63) | (0.24–0.32) | (0.37–0.42) | (0.37–0.55) |
| Frontal Cortex | 0.70 | 0.26 | 0.43 | 0.48 |
|  | (0.65–0.78) | (0.23–0.29) | (0.38–0.47) | (0.42–0.53) |
| Cerebellum | 0.29 | 0.18 | 0.21 | 0.12 |
|  | (0.28–0.31) | (0.16–0.20) | (0.18–0.26) | (0.11–0.28) |
| Hypothalamus | 0.77 | 0.23 | 0.38 | 0.53 |
|  | (0.69–0.83) | (0.18–0.27) | (0.34–0.41) | (0.44–0.60) |
| Brain | 0.61 | 0.27 | 0.39 | 0.40 |
|  | (0.56–0.63) | (0.24–0.30) | (0.37–0.42) | (0.32–0.50) |
| Hypothal/(CB) | 2.7 | 1.3 | 1.8 | 4.4 |
| Striatum/(CB) | 2.1 | 1.6 | 1.9 | 3.8 |

It will be understood that compounds of the invention can be labeled with an isotope of any atom or combination of atoms in the structure. While $^{18}$F has been emphasized herein as being particularly useful for PET imaging, other uses are contemplated and will be apparent to those skilled in the art. For example, without limitation, compounds of the invention can be labeled with $^{14}$C to provide a tracer useful for biochemical studies of serotonin transporter. In addition, the binding studies reported herein demonstrate a pharmacological effect of compounds of the invention which can be utilized for physiological and behavioral studies and therapies, as will be apparent to those skilled in the art.

All references cited in this application are specifically incorporated in their entirety by reference herein.

We claim:

1. A compound of the formula:

Wherein X is —CH$_2$CH$_2$Q, —CHCHR or —CFCH$_2$ and Q is F or CH$_2$F, R is I or CH$_2$F; Y is selected from a group consisting of H, F, Cl, Br and I.

2. The compound of claim 1 wherein at least one halogen is selected from the group consisting of $^{18}$F, $^{123}$I, $^{125}$I, $^{131}$I, $^{75}$Br, $^{76}$Br, $^{77}$Br, and $^{82}$Br.

3. The compound of claim 1 wherein X is CH$_2$CH$_2$F or CH$_2$CH$_2$$^{18}$F.

4. The compound of claim 1 wherein X is CH$_2$CH$_2$CH$_2$F or CH$_2$CH$_2$CH$_2$$^{18}$F.

5. The compound of claim 1 wherein X is CFCH$_2$ or C$^{18}$FCH$_2$.

6. The compound of claim 1 wherein X is CHCHI.

7. The compound of claim 1 wherein X is selected from the group consisting of CHCH$^{123}$I, CHCH$^{125}$I and CHCH$^{131}$I.

8. The compound of claim 1 wherein X is CHCHCH$_2$F or CHCHCH$_2$$^{18}$F.

9. The compound of claim 1 wherein X is CCH$_2$CH$_2$F or CCH$_2$CH$_2$$^{18}$F.

10. The compound of claim 3 wherein Y is Br.

11. The compound of claim 3 wherein Y is Cl.

12. The compound of claim 6 wherein Y is H.
13. The compound of claim 7 wherein Y is H.
14. The compound of claim 8 wherein Y is H.
15. The compound of claim 9 wherein Y is H.
16. The compound of claim 12 wherein said compound is a Z isomeric form.
17. The compound of claim 13 wherein said compound is a Z isomeric form.
18. The compound of claim 14 wherein said compound is a Z isomeric form.
19. A kit for rapid synthesis of a radioactively labeled compound, comprising (a) a compound having the structure:

wherein L is a leaving group which is displaced by a substituent containing a radiotracer atom, wherein said substituent is $CH_2CH_2Q$, CHCHR or $CFCH_2$ where Q is $^{18}F$ or $CH_2{}^{18}F$ and R is $^{123}I$, $^{125}I$, $^{131}I$, or $CH_2{}^{18}F$, (b) a reagent capable of displacing said L with said substituent.

20. A method of conducting positron emission tomography or single photon emission tomography imaging of a subject comprising administering to said subject an image-generating amount of a compound according to claim 1 which contains at least one radioactive halogen, and measuring the distribution within the subject of said compound by positron emission tomography or single photon emission tomography.

21. The method of claim 20 wherein the halogen is selected from the group consisting of $^{76}Br$, $^{75}Br$, and $^{18}F$, and the distribution of the compound measured by positron emission tomography.

22. A method for conducting single photon emission imaging of a subject comprising administering to said subject an image-generating amount of a compound according to claim 1 which contains at least one radioactive halogen, and measuring the distribution within the subject of said compound by single photon emission tomography.

23. A method according to claim 22 wherein the compound of claim 1 contains at least one of the following: $^{75}Br$, $^{77}Br$, $^{123}I$ or $^{131}I$, and measuring the distribution within the subject of said compound by single photon emission tomography.

* * * * *